United States Patent [19]

Saito et al.

[11] 4,356,326

[45] Oct. 26, 1982

[54] PROCESS FOR PRODUCING 3-OXOCYCLOPENTENES

[75] Inventors: Kenji Saito, Sonehigashi; Hiroshi Yamachika, Osaka, both of Japan

[73] Assignee: Sumitomo Chemical Company, Limited, Osaka, Japan

[21] Appl. No.: 213,632

[22] Filed: Dec. 5, 1980

[30] Foreign Application Priority Data

Dec. 6, 1979 [JP] Japan .................................. 54-158817
May 16, 1980 [JP] Japan .................................. 55-65771

[51] Int. Cl.³ .................... C07C 45/47; C07C 49/573
[52] U.S. Cl. .................................. 568/322; 568/361; 568/379
[58] Field of Search .................... 568/322, 361, 379

[56] References Cited

U.S. PATENT DOCUMENTS

3,628,970 12/1971 Stephens et al. .................. 568/379
3,947,519 3/1976 Matsui et al. .................... 568/379
4,107,181 8/1978 Evans ............................. 568/379

FOREIGN PATENT DOCUMENTS

53-127462 6/1978 Japan .............................. 560/122

OTHER PUBLICATIONS

Piancatelli et al., Tet. Let., vol. 1976, pp. 3555-3558, (1976).
Piancatelli et al., Tet. Let. vol. 1977, pp. 1131-1134, (1977).
Piancatelli et al., Tetrahedron, vol. 34, pp. 2275-2278, (1978).
Scettri et al., Tetrahedron, vol. 35, pp. 135-138, (1979).
Mamdopur et al., Chem. Abst., vol. 92, #197,966y, (1980).

*Primary Examiner*—James H. Reamer

*Attorney, Agent, or Firm*—Birch, Stewart, Kolasch & Birch

[57] ABSTRACT

A process for producing 3-oxocyclopentenes which comprises treating a furan-carbinol of the formula:

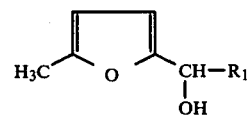

wherein $R_1$ is an alkyl group having not more than 6 carbon atoms, an alkenyl group having not more than 6 carbon atoms, an alkynyl group having not more than 6 carbon atoms or a group of the formula:

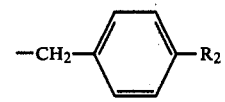

in which $R_2$ is a hydrogen atom, a methyl group or a halogen atom in an aqueous medium in the presence or absence of a catalyst at a pH of 3 to 6.5 to give the corresponding 3-oxocyclopentene of the formula:

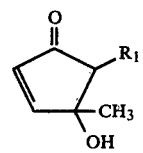

wherein $R_1$ is as defined above.

3 Claims, No Drawings

PROCESS FOR PRODUCING 3-OXOCYCLOPENTENES

The present invention relates to a process for producing 3-oxocyclopentenes. More particularly, it relates to a novel and improved process for preparing 3-oxocyclopentenes of the formula:

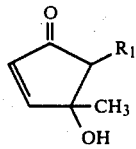

(I)

wherein $R_1$ is an alkyl group having not more than 6 carbon atoms (e.g. methyl, propyl, hexyl, cyclohexyl), an alkenyl group having not more than 6 carbon atoms (e.g. allyl), an alkynyl group having not more than 6 carbon atoms (e.g. propargyl) or a group of the formula:

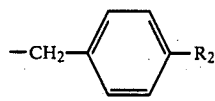

wherein $R_2$ is a hydrogen atom, a methyl group or a halogen atom (e.g. chlorine, bromine, fluorine).

The 3-oxocyclopentenes of the formula (I) are useful as intermediates for the production of agricultural chemicals, medicines (e.g. prostaglandin), perfumes (e.g. jasmone), etc.

For preparation of the 3-oxocyclopentenes (I), there has been hitherto adopted a method comprising the following reaction [G. Piancatelli et al.: Tetrahedron, 34, 2775–2778 (1978)]:

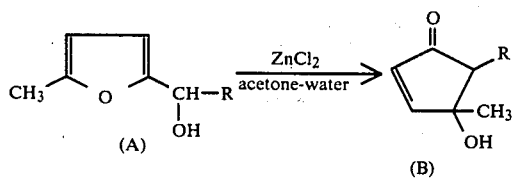

However, the applicability of this method is greatly influenced by the kind of the substituent R. When, for instance, it represents phenyl, 2-thienyl or p-tolyl, the 3-oxocyclopentene (B) is readily obtainable in a good yield within a short reaction time. When, for instance, it represents lower alkyl, lower alkenyl, lower alkynyl, benzyl or substituted benzyl, a long reaction time is required, and the yield of the objective 3-oxocyclopentene (B) is extremely low.

As the result of an extensive study, it has now been unexpectedly found that the treatment of the furan-carbinol (A) in an aqueous medium within a certain specific pH range can afford the corresponding 3-oxocyclopentene (B) in a good yield within a short reaction time even when the furan-carbinol (A) is of the kind to which the said known method could be hardly applied.

According to the present invention, there is provided a process for preparing the 3-oxocyclopentenes (I) from the corresponding furan-carbinols of the formula:

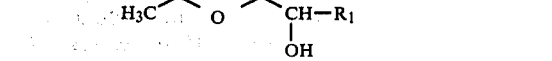

(II)

wherein $R_1$ is as defined above, characterized in that the latter is treated in an aqueous medium at a pH of 3 to 6.5.

The characteristic feature of the process of this invention resides in that the treatment is effected in an aqueous medium at a pH of 3 to 6.5. As the aqueous medium, there may be used water alone or water containing a small proportion of any organic solvent (e.g benzene, toluene, xylene, diisopropyl ether, acetone, tetrahydrofuran, dioxane). The amount of the aqueous medium to be used may be usually from 0.5 to 200 parts by weight, preferably from 5 to 100 parts by weight, to one part by weight of the starting furan-carbinol (II).

The pH value of the reaction system is required to be maintained between 3 and 6.5, preferably between 3 and 6, and most preferably between 3.5 and 5.8. When the pH value is higher than the said upper limit, the reaction rate becomes markedly small or slow. When the pH value is lower than the said lower limit, side reactions proceed so that the yield of by-products is increased. As the acidic and/or basic substance for regulation of the pH value, any usual acidic or basic substance may be employed. Examples of the acidic substance are inorganic acids (e.g. sulfuric acid, hydrochloric acid, nitric acid), organic acids (e.g. acetic acid, p-toluenesulfonic acid), acidic metal salts (e.g. sodium dihydrogenphosphate, sodium hydrogensulfite), acid ion-exchange resins, etc. Examples of the basic substance are hydroxides of alkali metals (e.g. sodium, potassium) and alkaline earth metals (e.g. calcium, barium), basic salts of said metals such as carbonates, bicarbonates and acetates, amines (e.g. triethylamine, pyridine), basic ion-exchange resins, etc. Buffer solutions containing these acidic or basic substances are also usable.

The treatment in the process of this invention is usually carried out at a temperature of 20° to 120° C., preferably of 80° to 100° C.

During the treatment, a metal salt or a surfactant may be incorporated into the reaction system for the purpose of shortening the reaction time, enhancing the yield, improving the volume efficiency, etc. Examples of the metal salt are magnesium salts (e.g. magnesium chloride, magnesium bromide, magnesium sulfate, magnesium nitrate, magnesium acetate), manganese salts (e.g. manganese chloride, manganese nitrate), copper salts (e.g. copper sulfate, copper acetate), zinc salts (e.g. zinc chloride), cobalt salts, iron salts, nickel salts, etc. The amount of the metal salt is usually from 0.001 to 0.2 mol, preferably from 0.01 to 0.05 mol, to 1 mol of the furan-carbinol (II). As the surfactant, any of the cationic, nonionic and amphoionic substances may be employed. The amount of the surfactant is usually from 0.1 to 20% by weight, preferably from 1 to 5% by weight, based on the weight of the furan-carbinol (II).

Practically, the treatment of this invention may be carried out by dissolving or suspending the furan-carbinol (II) into an aqueous medium containing or not any of a metal salt and a surfactant, elevating the temperature to a preferred temperature and causing the proceeding of the reaction while controlling the pH value between 3 and 6.5. When the production amount of the 3-oxocyclopentene (I) reaches the maximum, the reaction is finished.

The, the starting furan-carbinol (II) may be prepared, for instance, by the reaction of 5-methylfurfural with a Grignard's reagent of the formula: $R_1MX$ wherein $R_1$ is as defined above, M is Mg, Zn or $Al_{2/3}$ and X is a halogen atom.

The present invention will be hereinafter explained further in detail by the following Examples.

EXAMPLE 1

In a reaction vessel, water (1 liter) and 5-methyl-2-furylallylcarbinol (25 g) were charged, and the pH value was adjusted to 5.5 with an aqueous 1 N NaOH solution and an aqueous 1 N HCl solution. The temperature was elevated up to 100° C. to reflux, and the mixture was stirred under reflux for 12 hours while maintaining a pH value of 5.0 to 5.5 by the addition of an aqueous 1 N NaOH solution and an aqueous 1 N HCl solution. After cooling to 40° C., the reaction mixture was neutralized with an aqueous 1 N NaOH solution, and sodium chloride (300 g) was added thereto. The mixture was extracted with toluene (100 ml) five times. From the extract, toluene was removed by distillation at 60° C. under reduced pressure to give an oily substance (23 g), which was subjected to distillation under reduced pressure to obtain 2-allyl-3-hydroxy-3-methyl-4-cyclopentenone (21.3 g). Yield, 85.2%. B.P., 77° C./0.1 mmHg. NMR spectrum (CCl$_4$, internal standard TMS, δ ppm, 60 MHz): 7.32 (d, 1H, 4-H); 5.92 (d, 1H, 5-H); 5.81 (complex m, 1H, —CH$_2$—C$\underline{H}$=CH$_a$H$_b$); 5.12 (m, 1H, —CH$_2$—CH=C$\underline{H}_a$H$_b$); 4.93 (m, 1H, —CH$_2$—CH=CH$_a$$\underline{H}_b$); 4.12 (broad s, 1H, 3-O$\underline{H}$); 2.37 (m, 3H, 2-H, s, —C$\underline{H}_2$—CH=CH$_a$H$_b$); 1.28 (s, 3H, 3—C$\underline{H}_3$).

EXAMPLE 2

In a reaction vessel, water (1600 ml), anhydrous sodium acetate (0.4 g) and 5-methyl-2-furylpropargylcarbinol (20 g) were charged, and the temperature was elevated to reflux. The pH value was adjusted to 4.5 with an aqueous 0.5 N acetic acid solution, and the mixture was stirred under reflux for 13 hours while maintaining a pH value of 4.0 to 5.0 by the addition of an aqueous ⅓ N NaOH solution. Then, the reaction mixture was cooled to 40° C., neutralized with an aqueous ⅓ N NaOH solution and, after addition of sodium chloride (300 g), extracted with methyl isobutyl ketone (400 ml) five times. From the extract, methyl isobutyl ketone was removed by distillation at 60° c. under reduced pressure to give an oily substance (16 g), which was subjected to distillation under reduced pressure to obtain 2-propargyl-3-hydroxy-3-methyl-4-cyclopentenone (14.8 g). Yield, 74%. B.P., 115°–132° C./0.1 mmHg. n$_D^{25}$ 1.5124. C$^{13}$ NMR spectrum (CDCl$_3$, internal standard TMS, δ ppm, 22.6 MHz): 206.2 (1-C); 167.8 (5-C); 130.7 (4-C); 82.0 (—CH$_2$—$\underline{C}$≡CH); 78.5 (3-C); 70.6 (—CH$_2$—C≡$\underline{C}$H); 57.0 (2-C); 23.4 (—$\underline{C}$H$_3$); 14.7 (—$\underline{C}$H$_2$—C≡CH).

EXAMPLE 3

In a reaction vessel, water (40 ml) and 5-methyl-2-furyl-n-butylcarbinol (0.5 g) were charged, and the pH value was regulated to 5 with an aqueous 1 N NaOH solution and an aqueous 1 N HCl solution. The temperature was elevated up to 100° C. to reflux, and the mixture was stirred under reflux for 30 hours while maintaining a pH value of 5 to 5.5 by the addition of an aqueous 1 N NaOH solution and an aqueous 1 N HCl solution. After cooling to 40° C., the reaction mixture was neutralized with an aqueous 1 N NaOH solution, and sodium chloride (12 g) was added thereto. The mixture was extracted with toluene (40 ml) five times. From the extract, toluene was removed by distillation at 60° C. under reduced pressure to give an oily substance (0.48 g), which was subjected to a thin layer chromatography on silica gel with a mixture of ethyl acetate-n-hexane (1:2 by volume) as the developing solvent. The objective part of the silica gel layer was collected by scraping and eluted with ethyl acetate. The silica gel was eliminated by filtration, and the filtrate was concentrated to obtain 2-n-butyl-3-hydroxy-3-methyl-4-cyclopentenone (3.5 g). Yield, 70%. NMR spectrum (CCl$_4$, internal standard TMS, δ ppm, 60 MHz): 7.25 (d, 1H, 4-H); 5.85 (d, 1H, 5-H); 3.63 (broad s, 1H, 3—O$\underline{H}$); 2.20 (m, 1H, 2-H); 1.25 (s, 3H, 3-C$\underline{H}_3$).

EXAMPLES 4 TO 13

Using the furan-carbinol (II), the corresponding 3-oxocyclopentene (I) was prepared in the same manner as in Example 1 under the conditions shown in the following Table:

| Example No. | Furan-carbinol (II) R$_1$ | Amount (g) | Amount of solvent (ml) | pH | Reaction time (hr) | Yield of product*[1] (%) |
|---|---|---|---|---|---|---|
| 4 | Methyl | 5 | 100 | 4.0–5.5 | 16 | 66 |
| 5 | Ethyl | 5 | 100 | 4.0–5.5 | 16 | 68 |
| 6 | Propyl | 0.5 | 40 | 4.0–5.3 | 30 | 76 |
| 7 | n-Hexyl | 0.5 | 40 | 4.0–5.6 | 30 | 78 |
| 8 | 2-Isoamyl | 0.5 | 40 | 4.0–5.5 | 30 | 70 |
| 9 | Isobutyl | 0.5 | 40 | 4.0–5.5 | 30 | 68 |
| 10 | 3-Butenyl | 1 | 40 | 4.0–5.5 | 30 | 70 |
| 11 | Benzyl | 0.5 | 40 | 4.0–5.4 | 30 | 89 |
| 12 | p-Methylbenzyl | 0.5 | 40 | 4.0–5.7 | 30 | 85 |
| 13 | p-Chlorobenzyl | 0.5 | 40 | 4.0–5.7 | 30 | 88 |

Note:
*[1] In Examples 6, 7, 12 and 13, isolation was effected by column chromatography.

EXAMPLE 14

In a reaction vessel, water (750 ml) was charged, and the temperature was elevated up to 100° C. to reflux. Then, 5-methyl-2-furylallylcarbinol (24 g) and a solution of MgCl$_2$.6H$_2$O (31.5 g) in water (160 ml) were dropwise added thereto in 2.5 hours and 3.5 hours, respectively. During the addition, the pH value of the reaction mixture was maintained at 5.7 to 5.3 by the addition of an aqueous 10% potassium primary phosphate solution and an aqueous 1 N NaOH solution.

After about 1.5 hours from the start of the reaction, the pH value stabilized and remained within said range. After completion of the addition of the aqueous MgCl₂ solution, the reaction mixture was stirred at pH 5.5 under reflux at 100° C. for an additional 4.5 hours. Then, the reaction mixture was cooled to 40° C. and neutralized with an aqueous 1 N NaOH solution. After addition of sodium chloride (320 g), the mixture was extracted with toluene (250 ml) four times. The extract was dried over anhydrous magnesium sulfate, and toluene was removed therefrom by distillation at 60° C. under reduced pressure to give an oily substance (21.6 g), which was subjected to distillation under reduced pressure to obtain 2-allyl-3-hydroxy-3-methyl-4-cyclopentenone (20.4 g). Yield, 85%. B.P., 88°–90° C./0.5 mmHg.

EXAMPLE 15

In a reaction vessel, water (150 ml) and tri-n-octylmethylammonium chloride (450 mg) were charged, and the pH value was adjusted to 5.5 with an aqueous ⅓ N HCl solution and an aqueous ⅓ N NaOH solution. Then, 5-methyl-2-furylallylcarbinol (11.0 g) was added thereto, and the temperature was elevated up to 100° C. to reflux. The mixture was stirred under reflux for 7 hours while maintaining a pH value of 5 to 5.5 by the addition of an aqueous ⅓ N NaOH solution and an aqueous ⅓ N HCl solution. After cooling to 40° C., sodium chloride (30 g) was added, and the mixture was extracted with toluene (70 ml) five times. From the extract, toluene was removed by distillation at 60°C. under reduced pressure to give an oily substance (10.1 g), which was subjected to chromatography on silica gel (100 g) with a mixture of ethyl acetate-n-hexane (1:2 by volume) as the developing solvent to obtain 2-allyl-3-hydroxy-3-methyl-4-cyclopentenone (7.1 g). Yield, 64.5%.

What is claimed is:
1. 2-Propargyl-3-hydroxy-3-methyl-4-cyclopentenone.

2. A process for producing 3-oxocyclopentenes which comprises treating a furan-carbinol of the formula:

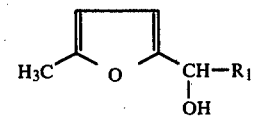

wherein R₁ is an alkyl group having not more than 6 carbon atoms, an alkenyl group having not more than 6 carbon atoms, an alkynyl group having not more than 6 carbon atoms or a group of the formula:

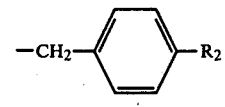

in which R₂ is a hydrogen atom, a methyl group of a halogen atom in a water medium at a pH of 3 to 6.5 and at a temperature of 20° to 120° C. to give the corresponding 3-oxocyclopentene of the formula:

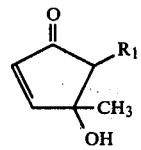

wherein R₁ is as defined above.

3. The process according to claim 2, wherein the treatment is effected in the presence of a catalyst selected from the group consisting of magnesium salts, manganese salts, copper salts, zinc salts, cobalt salts, iron salts, nickel salts, cationic surfactants, nonionic surfactants and amphionic surfactants.

* * * * *